US009452266B2

(12) United States Patent
Roervig (10) Patent No.: US 9,452,266 B2
(45) Date of Patent: Sep. 27, 2016

(54) INJECTION PEN WITH MECHANICAL DOSE DISPLAY COMPRISING LARGE CIPHERS (71) Applicant: Novo Nordisk A/S, Bagsvaerd (DK)

(72) Inventor: Simon Roervig, Copenhagen OE (DK)

(73) Assignee: Novo Nordisk A/S, Bagsvaerd (DK)

( * ) Notice: Subject to any disclaimer, the term of this patent is extended or adjusted under 35 U.S.C. 154(b) by 340 days.

(21) Appl. No.: 14/364,528

(22) PCT Filed: Dec. 10, 2012

(86) PCT No.: PCT/EP2012/074965
§ 371 (c)(1),
(2) Date: Jun. 11, 2014

(87) PCT Pub. No.: WO2013/087574
PCT Pub. Date: Jun. 20, 2013

(65) Prior Publication Data
US 2014/0323974 A1 Oct. 30, 2014

Related U.S. Application Data (60) Provisional application No. 61/576,395, filed on Dec. 16, 2011.

(30) Foreign Application Priority Data

Dec. 14, 2011 (EP) ..................... 11193431

(51) Int. Cl.
*A61M 5/315* (2006.01)
*A61M 5/24* (2006.01)
*A61M 5/31* (2006.01)

(52) U.S. Cl.
CPC ........... *A61M 5/31573* (2013.01); *A61M 5/24* (2013.01); *A61M 5/3156* (2013.01);

(Continued)

(58) Field of Classification Search
CPC ............... A61M 5/31533; A61M 5/31548; A61M 5/3155; A61M 5/31551; A61M 5/31553; A61M 5/31556; A61M 5/31558; A61M 5/3156; A61M 5/31563
See application file for complete search history.

(56) References Cited

U.S. PATENT DOCUMENTS 5,279,585 A 1/1994 Balkwill
5,316,239 A 5/1994 Sugawara
(Continued)

FOREIGN PATENT DOCUMENTS

CN 101084028 A 12/2007
CN 101370540 A 2/2009
(Continued)

*Primary Examiner* — Kevin C Sirmons
*Assistant Examiner* — William Carpenter
(74) *Attorney, Agent, or Firm* — Wesley Nicolas (57) ABSTRACT The present invention relates to an injection device (1) having a mechanical dose size display wherein a first scale drum (10) carrying a series of first ciphers (11) and a second scale drum (20) carrying a series of second ciphers (21) are both rotatable able and axially moveable relatively to a housing (2) of the injection device in such a way that one of the first ciphers (11) and one of the a second ciphers (21) appears simultaneously in a window provided in the housing (2) thereby informing the user of the set dose. Both the first scale drum (10) and the second drum (20) preferable carries five ciphers (11, 21) around one full circumferential perimeter. The ciphers (11, 21) are provided in different circumferential circles and/or helically provided.

10 Claims, 6 Drawing Sheets (52) U.S. Cl.
CPC .... *A61M 5/31551* (2013.01); *A61M 5/31553* (2013.01); *A61M 5/31558* (2013.01); *A61M 5/31593* (2013.01); *A61M 5/31528* (2013.01); *A61M 2005/3126* (2013.01)

(56) References Cited

U.S. PATENT DOCUMENTS

| | | | |
|---|---|---|---|
| 5,921,966 A * | 7/1999 | Bendek | A61M 5/24 |
| | | | 604/207 |
| 5,961,495 A * | 10/1999 | Walters | A61M 5/31553 |
| | | | 604/111 |
| 7,214,213 B2 | 5/2007 | Michel et al. | |
| 8,202,255 B2 * | 6/2012 | Saiki | A61M 5/31551 |
| | | | 604/181 |
| 9,108,002 B2 * | 8/2015 | Markussen | A61M 5/20 |
| 2001/0053894 A1 * | 12/2001 | Steenfeldt-Jensen | A61M 5/31553 |
| | | | 604/211 |
| 2006/0167419 A1 | 7/2006 | Fiechter et al. | |
| 2007/0233015 A1 | 10/2007 | Saiki | |
| 2010/0274198 A1 | 10/2010 | Bechtold | |
| 2011/0313365 A1 * | 12/2011 | Wieselblad | A61M 5/31525 |
| | | | 604/207 |

FOREIGN PATENT DOCUMENTS

| | | |
|---|---|---|
| EP | 1819382 | 8/2007 |
| JP | 2000-070368 A | 3/2000 |
| WO | 9311813 | 6/1993 |
| WO | 01/87386 A1 | 11/2001 |
| WO | 2004/020028 A1 | 3/2004 |
| WO | 2008/148864 A1 | 12/2008 |
| WO | 2010084164 A1 | 7/2010 |
| WO | 2010089417 A2 | 8/2010 |
| WO | 2010097125 A1 | 9/2010 |
| WO | 2011067267 A1 | 6/2011 |
| WO | 2012/130991 A1 | 10/2012 |

* cited by examiner

INJECTION PEN WITH MECHANICAL DOSE DISPLAY COMPRISING LARGE CIPHERS

CROSS-REFERENCE TO RELATED APPLICATIONS

This application is a 35 U.S.C. §371 National Stage application of International Application PCT/EP2012/074965 (published as WO 2013/087574), filed Dec. 10, 2012, which claimed priority of European Patent Application 11193431.1, filed Dec. 14, 2011; this application claims priority under 35 U.S.C. §119 of U.S. Provisional Application 61/576,395; filed Dec. 16, 2011.

THE TECHNICAL FIELD OF THE INVENTION

The invention relates to an injection device with a large display and especially to a purely mechanical injection device with the ability to display the dose setting size in large ciphers.

DESCRIPTION OF RELATED ART

Many known injection devices and especially pen shaped injection devices have a limited space for the ciphers displaying the dose set by the user.

An injection device in which the dose display is formed as a traditional odometer is disclosed in EP 1,819,382. In one embodiment, the dose display is constructed from two wheels each carrying the ten ciphers from "0" to "9" such that the two wheels together can form all numbers from "00" to "99" in the window of the housing. The second wheel carrying the "ten" ciphers is rotated one increment equal to one tenth of a revolution or 36 degree every time the first wheel carrying the "ones" ciphers is rotated one full revolution (=360 degree) such that the second wheel counts the number of full revolutions of the first wheel. Neither of the two wheels is moved axially during dose setting and as a consequence the maximum physical height of a cipher is less than one tenth part of the circumferential perimeter.

Further developments of odometer-like solutions are disclosed in WO 93/11813, WO 2008/148864 and US 2007/0233015.

In WO 93/11813 a rotatable scale carrying the "ones" ciphers are rotated and axially moved relatively to a fixed scale carrying the "tens" ciphers during dose setting. In this solution the "ones" ciphers only show even numbers which means that a user can only set the dose size in two-increment steps. In order to obtain a more optimal treatment, people suffering from e.g. diabetes today expect injection devices to at least operate in one-increment steps.

Such one-increment injection device is disclosed in US 2007/0233015 where the "tens" ciphers are provided in connection with a scale drum that both rotate and move axially relatively to the housing during dose setting. The "tens" ciphers are printed directly on the scale drum and the "ones" ciphers are provided on a ring-shaped element, which rotate without any axial displacement. It is thus necessary to rotate the scale drum and the "ones" ring-shaped element one full revolution i.e. 360 degrees in order for the "tens" to count one "ten" digit up (or down, if rotated in the opposite direction) as there is 10 identical "tens" printed on 360 degrees of the helically movable scale drum.

A similar one-increment injection device is disclosed in WO 2008/148864. In this injection device the "tens" ciphers are printed on an element which is pulled axially by the rotation of the metering drum and the "ones" ciphers are provided on a ring-shaped element, which rotate without any axial displacement. Whenever the ring-shaped element is rotated a full revolution, or in one embodiment, half a revolution, the "tens" element is moved axially by its engagement with a track in the metering drum.

A common feature for all these odometer-like solutions is that the "tens" element counts each full revolution of the "ones" element and that the ten ciphers from "0" to "9" is equally distributed over the circumferential perimeter of the "ones" element.

The visibility of the dose indication is thus rather limited as each cipher can never stretch over more than maximum a tenth part of the perimeter equal to 36 degrees of the circumferential perimeter of the usually pen-shaped injection device. This makes it difficult for people with impaired sight to visible inspect the size of dose setting of the injection device.

DESCRIPTION OF THE INVENTION

It is an object of the present invention to provide an injection device in which the size of the individual ciphers indicating the set dose can be increased to enhance visibility. It is further an object to provide a large cipher indicator suitable to be implemented in a mechanical pen-shaped injection device.

The invention is defined in claim 1.

Accordingly in one aspect the present invention relate to a mechanical dose size display for displaying the size of the dose intended for injection that the user selects. The setting of the dose is done by rotating a dose setting member which preferably is located at a proximal end of a pen-shaped injection device.

The dose size display comprises two different scale drums each carrying a series of ciphers. One scale drum preferably carries the "tens" ciphers and the other scale drum preferably carries the "ones" ciphers. When the "ones" scale drum changes position from "9" to "0" it preferably triggers the "tens" scale drum to count one cipher up thus making it possible to display any number from "00" to "99". For injection devices incorporating a dial-down mechanism, the display mechanism also works when dialing in the downward direction. The ciphers or indicia, which can be different from Arabian ciphers, can be printed directly on the scale drums or they can be applied in alternative ways.

Each scale drum is rotatable mounted with respect to the housing of the injection device and is further configured such that they can both move axially relatively to the housing when rotated. One scale drum is preferably helically guided and the other is axially and oscillating guided. The oscillating scale drum is not necessarily configured such that it respond with a constant axial oscillating movement during the rotation, but is mounted such that it at least perform one axial oscillating movement for each full rotation.

Due to the axial movement of the scale drums during rotation, the ciphers can be provided axially displaced which makes it possible to increase the size of the ciphers when compared to ciphers on a scale display element which do not move axially during rotation.

In one embodiment, the first scale drum surrounds the second scale drum. In order to obtain a compact pen design one scale drum is preferably mounted inside the other scale drum. The outer—first-scale drum is thus provided with openings through which the user can visible see the ciphers carried on the inner—second-scale drum. "Opening" is meant to be an "optical opening" i.e. it covers an actual psychical opening or alternatively an area through which a user can visible inspect the inner scale drum. Such area can e.g. be provided by making a restricted area of the outer scale drum transparent. The inner drum is not necessarily fully concealed by the outer drum.

When a user sets the size of a dose to be injected this is done by rotating the proximally located dose setting button. This rotation is transferred to a rotation of the second scale drum which in turn transfers this rotation to rotation of the first scale drum. The means transferring such rotation from the second scale drum to the first scale drum can be expressed in many different ways. Preferably, a mechanism is provided between the second scale drum and the first scale drum such that the first scale drum is incrementally i.e. stepwise rotated when the second scale drum has been rotated for a number of full rotations. Like in a traditional odometer e.g. as disclosed in EP 1,819,382, the first scale drum incrementally counts the numbers of full rotations of the second scale drum. The annexed figures discloses an example of a particular way of designing such mechanism however it can be embodied in different ways as long as the first scale drum carrying the "tens" is rotated one increment for each number of full rotations of the second scale drum carrying the "ones". In the disclosed example, the first scale drum is rotated one increment for each two full revolutions of the second scale drum. This could e.g. be embodied by having a flexible element on the second scale drum that engages and incrementally moves the first scale drum for each two revolutions. This flexible element could engage the first scale drum either axially or radially once for each two full revolutions e.g. via a gearing mechanism such as a planet gear.

The second scale drum carrying the "ones" ciphers are guided in an oscillating track preferably but not necessarily provided in the housing. This track can follow different curves, however, in an embodiment in which the ciphers are distributed in two different rows each having five ciphers, the curve can be shaped similar to a sinus curve such that the scale drum oscillates axially and stepwise between the two rows of ciphers whenever rotated. This solution will increase the space that each cipher can occupy significantly since only five ciphers can now occupy 360 degrees. All though two rows each having five ciphers is preferred any convenient number of rows are possible. Other configurations of the track are also possible. The track can e.g. have a curve such that it only shifts between the two rows one time for each full rotation. The track is preferably endless such that continuous rotation of the second scale drum is possible. A similar oscillating mechanism (for a spinning reel) comprising such endless track is disclosed in principles in U.S. Pat. No. 5,316,239.

The first scale drum is helically guided. The "tens" ciphers are preferably provided numerically in a helical pattern on the first—outer-scale drum, which scale drum is guided in a helical track e.g. provided internally in the housing such that each time the "tens" scale drum is rotated it moves helically. Next to each "tens" cipher, an opening is provided through which the "ones" cipher on the second—inner-scale drum can be visible seen. A combination of one "tens" ciphers and an adjacent opening are thus brought consecutively into the area of the window in the housing since the helical track corresponds to the helical printing on the circumferential perimeter of the first scale drum.

A gearing is preferably provided between the dose setting button and the display mechanism. In one example the rotation of the scale drums are coupled to the rotation of the dose setting button through a planet-gearing mechanism.

In order for the first scale drum carrying the "tens" to rotate one increment every time the second scale drum has displayed the cipher "9", the two scale drums are coupled together such that a number of rotations of one of the scale drums results in a rotation of the other scale drum i.e. one scale drum counts the numbers of full rotations of the other scale drum. This does not necessarily mean it counts every full rotation; it can be designed to only count every second full rotation as in the disclosed example of the invention or any other number of rotations. The planet gear disclosed could e.g. be utilized to transfer this rotation from the second scale drum to the first scale drum thus counting the revolutions of the second scale drum, or an alternative kind of gearing mechanism between the two scale drums could be provided.

In an example using Arabian numbers the first scale drum carrying the "tens" ciphers must be rotated to a new "ten" cipher every time the second scale drum carrying the "ones" ciphers has displayed the cipher "9" and moves to the cipher "0". In the embodiment where the "ones" ciphers is provided in two rows each having five ciphers, the "tens" scale drum most be rotated to a higher (or lower if the dose is being reduced) "tens" cipher each time the "ones" scale drum has been rotated two full rotations i.e. for every 720 degrees of rotation.

This rotation of the "tens" scale drum is done by a clutch sleeve coupled between the two scale drums. The "ones" scale drum is thus provided with at least one guide pin which engages the clutch sleeve when it is time to rotate the "tens" scale drum. The clutch sleeve is keyed to the "tens" scale drum such that any rotation of the clutch sleeve results in a simultaneous rotation of the "tens" scale drum.

The guide pin is preferably forced to engage the clutch sleeve every time the "ones" scale drum has rotated two full rotations such that the "ones" scale drum rotate the clutch sleeve one incremental step resulting in the "tens" scale drum rotating to the next consecutive "tens" cipher.

The guide pin is preferably forced into engagement with the clutch sleeve by being lifted by a raised bar provided on a clutch guide which is inrotatable coupled to the housing or alternatively formed as a part of the housing. In one embodiment, the raised bar is located such that it lifts the guide pin into engagement with the clutch sleeve for each second full rotation of the second scale drum carrying the guide pin. The result being that the first scale drum is rotated one incremental step whenever the second scale drum has been rotated through two full revolutions. The incremental step being such that the consecutive "tens" cipher is brought into the range of the window.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

"Scale drum" is meant to be a cylinder shaped element carrying indicia indicating the size of the selected dose to the user of the injection pen. The cylinder shaped element making up the scale drum can be either solid or hollow. "Indicia" is meant to incorporate any kind of printing or otherwise provided symbols e.g. engraved or adhered symbols. These symbols are preferably, but not exclusively, Arabian numbers from "0" to "9". In a traditional injection pen configuration the indicia is viewable through a window provided in the housing.

"Cartridge" is the term used to describe the container containing the drug. Cartridges are usually made from glass but could also be moulded from any suitable polymer. A cartridge or ampoule is preferably sealed at one end by a pierceable membrane referred to as the "septum" which can be pierced e.g. by the back-end of a needle cannula. The opposite end is typically closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug. However, any kind of container—rigid or flexible—can be used to contain the drug.

Further the term "injection needle" defines a piercing member adapted to penetrate the skin of a subject for the purpose of delivering or removing a liquid.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device which usually carries the injection needle whereas the term "proximal end" is meant to refer to the opposite end pointing away from the injection needle and usually carrying the dose dial button.

Figure 1:
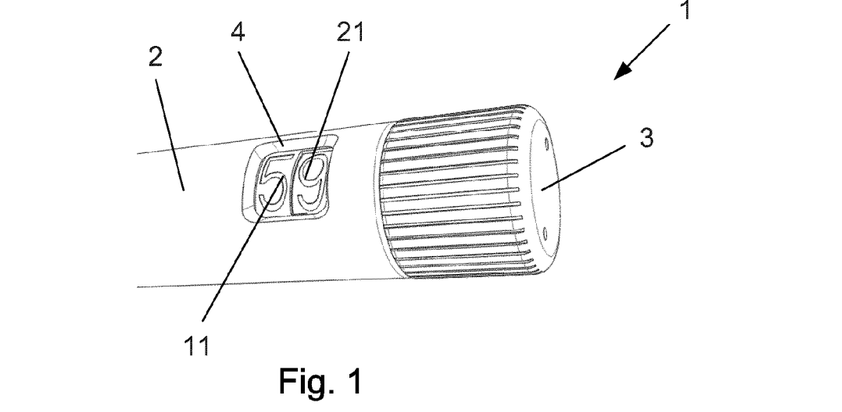
FIG. 1 show a perspective view of the injection pen according to the present invention.

FIG. 1 discloses the end of the injection pen 1 being proximal to the cartridge containing the drug. At the most proximal end of the housing 2 a dial button 3 is provided which a user can rotate to select a dose. The housing 2 is further provided with a window 4 through which the user can visible inspect the size of dose being dialed.

The size of the dose is visualized as a number made up from two ciphers 11, 21. A first cipher 11 indicates the first of the two ciphers 11, 21 in the two-digit number, hereafter named as the "tens". This first cipher 11 is followed by a second cipher 21 hereafter named as the "ones".

Figure 2:
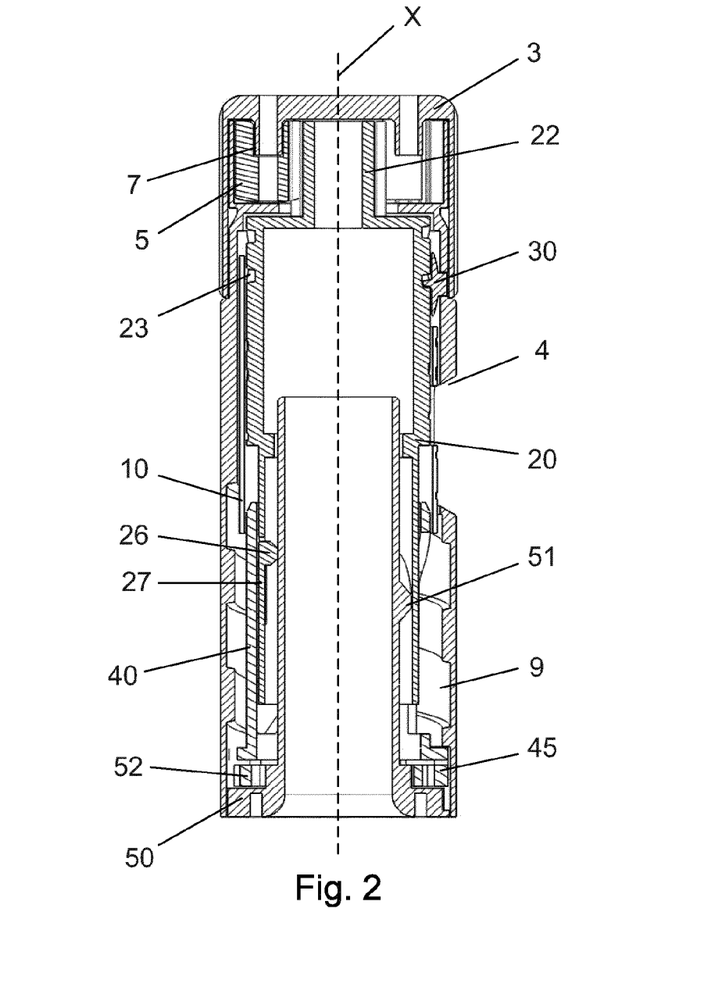
FIG. 2 show an cross sectional view of the dose setting mechanism of the injection pen.
Figure 3:
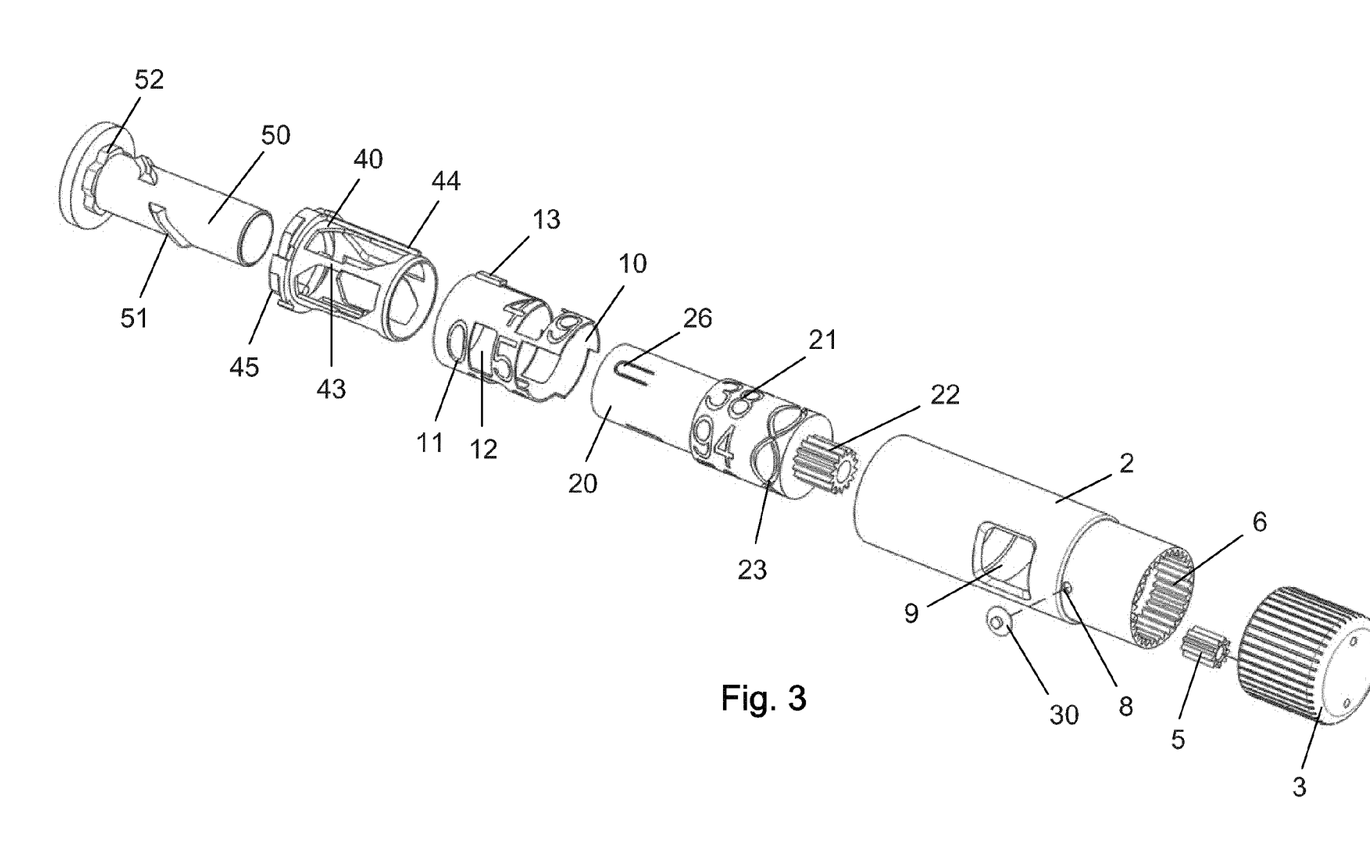
FIG. 3 show an exploded view of the dose setting mechanism of the injection pen.

As seen in FIGS. 2 and 3, the first cipher 11 is carried on a first scale drum 10 rotatable mounted in the housing 2 and the second cipher 21 is carried on a second scale drum 20 which is also rotatable mounted in the housing 2. The ciphers 11, 21 are preferably printed on the respective scale drum 11, 21.

Figure 6:
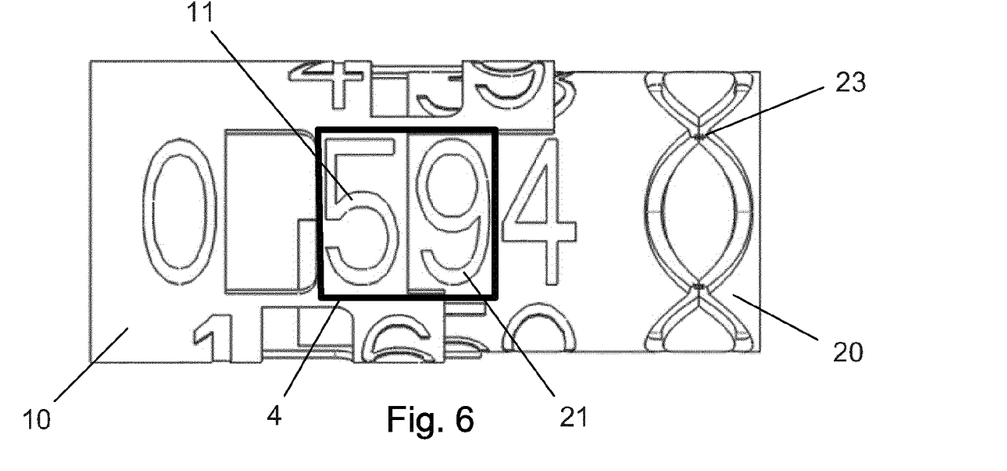
FIG. 6 show a view of the dose setting as appearing in the window.
Figure 7:
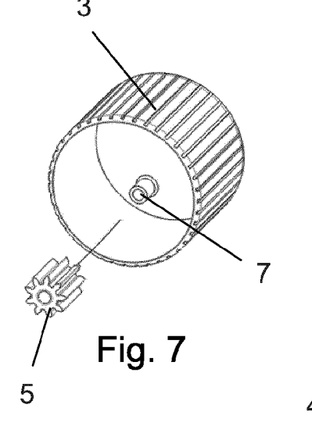
FIG. 7 show an exploded view of the planet gear mechanism.

The first cipher 11 on the first scale drum 10 comprises the numbers from "0" to "9". The first ciphers 11 are located helically dislocated as also depictured in FIG. 4. At the right hand side of each first cipher 11 an opening 12 in the first scale drum 10 is provided. The first scale drum 10 surrounds the second scale drum 20 such that the second cipher 21 on the second scale drum 20 can be viewed through the opening 12 in the first scale drum 10 as depicted in FIG. 6 thus forming a two-digit number. As can be seen in FIG. 6 and to be explained, the cipher "6" will be moved into the window 4 once the first scale drum 10 is rotated and moved axially resulting in a helical movement. Further the opening right next to the cipher "6" will be moved into position in the window 4 and the cipher "0" on the second scale drum 20 will become visible through that opening, such that the first scale drum 10 together with the second scale drum 20 will form the cipher "60".

The proximal end of the second scale drum 20 is provided with a toothed extension 22 which engages a gear wheel 5, which gear wheel 5 is coupled to the dose dial 3 eccentric to the centre axis X as depictured in FIG. 2. The gear wheel 5 is e.g. mounted on a shaft 7 provided eccentric to the centre axis X. The gear wheel 5 further engages a toothed ring 6 provided internally in the housing 2.

When a user dials a dose by rotating the dose dial 3, the second scale drum 20 rotate along with the dose dial 3 in the gearing ratio set by the planet gearing mechanism 3, 5, 6, 22.

Figure 8:
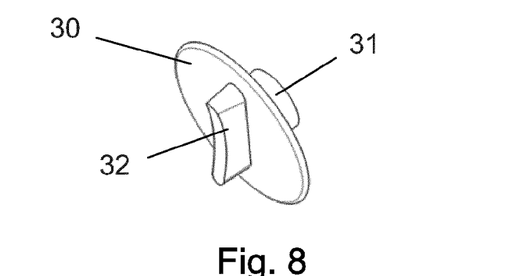
FIG. 8 show a perspective view of the guide pin.

The housing 2 is further provided with a guide pin 30 which is disclosed in details in FIG. 8. This guide pin 30 is provided internally in the housing 2 and connected to the housing 2 by having a circular extending protrusion 31 rotatable inserted in a hole or opening 8 provided in the wall of the housing 2. Opposite to the extending protrusion 31 and pointing towards the centre axis X of the injection pen 1 a keyway 32 is provided. This keyway 32 has a rectangular shape and engages a track 23 provided in the second scale drum 20.

Figure 5:
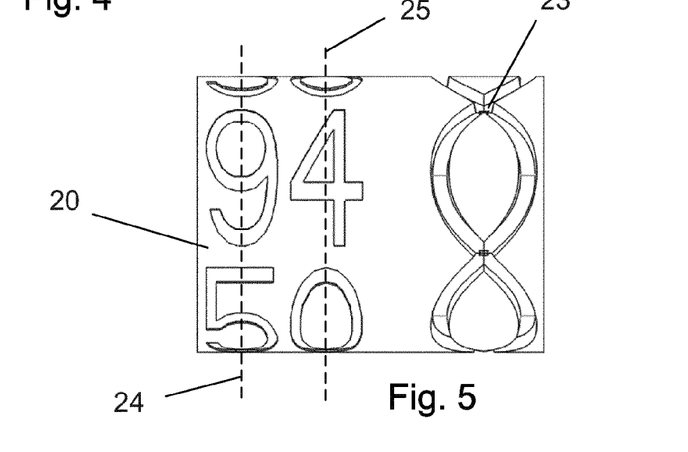
FIG. 5 show a view of the second scale drum.

FIG. 5 discloses the second scale drum 20. The track 23 is carved into the second scale drum 20 and follows a curve. As the keyway 31 of the guide pin 30 (secured in the housing 2) engages the track 23, the second scale drum 20 oscillates axially following the track 23 as it is rotated in the housing 2. The track 23 is an endless oscillating track such that the second scale drum 20 oscillates continuously when rotated relatively to the housing 2.

Figure 11A:
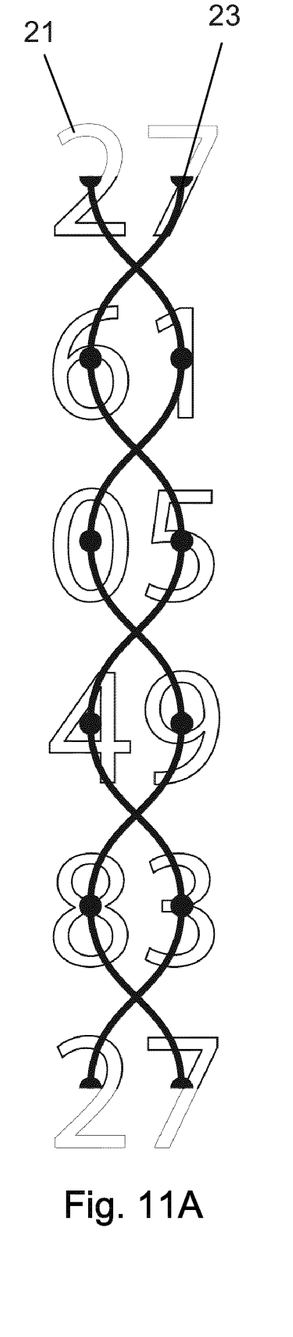
FIG. 11A-C show various lay-outs of the guiding track.
Figure 11B:
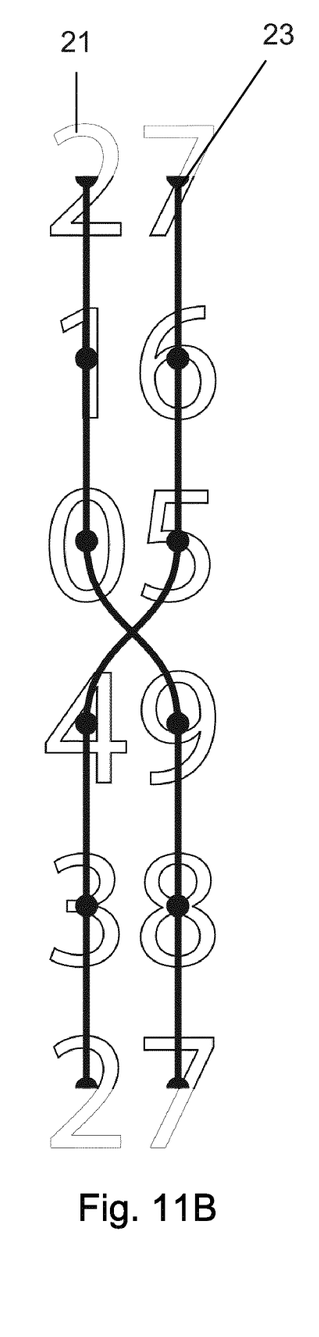
Figure 11C:
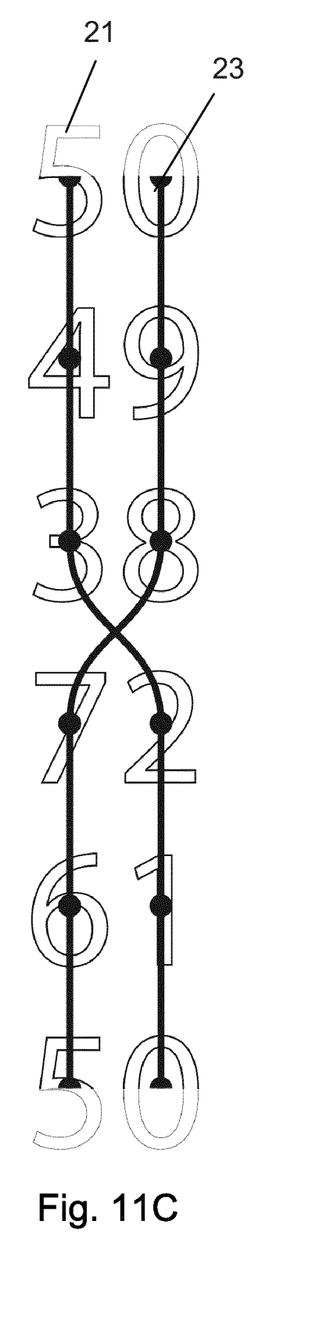

Various configurations of tracks 23 are depictured in FIG. 11A-C. The curve formed by the track 23 can be that of a sinus curve as in FIG. 11A, such that the "ones" ciphers 21 oscillates axially for each incremental rotation of the second scale drum 20 or it can be a curve only having two axial movements along the track 23 as depictured in FIG. 11B-C. The "ones" ciphers are located such that the consecutive numbering follows the profile of the curve.

As further disclosed in FIG. 5, the "ones" ciphers are located in two different rows around the periphery of the second scale drum 20.

In one embodiment (FIG. 11A), the odd ciphers (1, 3, 5, 7 and 9) is provided along a first circle 24 and the even ciphers 11 (2, 4, 6, 8, 0) is provided along a second circle 25. Since the "ones" ciphers 11 from "0" to "9" is provided in two different circles 24, 25 axially dislocated form each other, the size of each cipher 11 can be strongly increased. Each "ones" cipher 11 can have a size of one fifth of the circumferential perimeter i.e. double the size of the ciphers in an ordinary odometer which carries all the 10 different "ones" ciphers along the perimeter.

However, other configurations of curves for the "ones" ciphers 11 are disclosed in FIG. 11B-C where it will be noted that the "ones" ciphers 11 are placed in consecutive numbering following the profile of the curve of the track 23. In FIG. 11B the second scale drum 20 shifts axially when passing from "4" to "5" and when passing from "9" to "0". In FIG. 110 the second scale drum shifts axially when passing from "2" to "3" and again when passing from "7" to "8".

As the second scale drum 20 oscillates axially when incrementally rotated following the curve depictured in FIG. 11A, each "ones" cipher 11 will be brought into the visible field of the window 4 and shown continuously from "0" to "9" over and over again.

The first scale drum 10 rides in a helical thread 9 provided on the inside of the housing 2 and is rotated one "tens" increment every time the second scale drum 20 rotate two full revolutions i.e. for each 720 degrees rotation of the second scale drum 20 as explained below.

Figure 4:
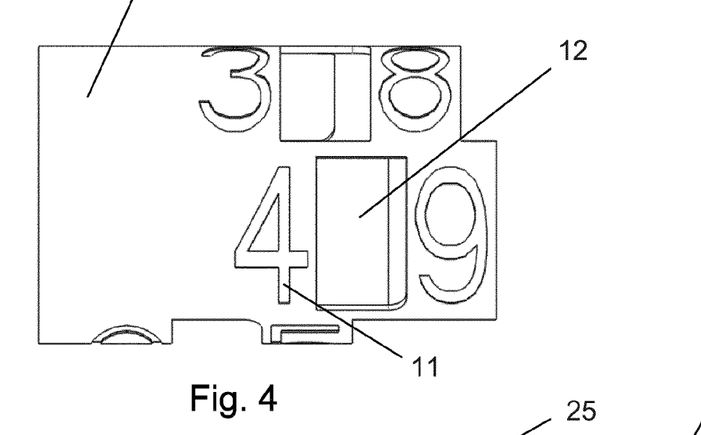
FIG. 4 show a view of the first scale drum.

The first scale drum 10 carries the "tens" ciphers 11 in a helical pattern as depictured in FIG. 4 and has an opening 12 provided at the right hand side of each "ten" ciphers 11 through which opening the "ones" ciphers 21 can be viewed as shown in FIG. 6. In this way all the numbers from "00" to "99" can be displayed continuously.

The first scale drum 10 is provided with a protrusion 13 extending perpendicular to the Centre axis X. This protrusion 13 engages the helical thread 9 internally in the housing 2 such that the first scale drum 10 is moved axially when rotated resulting in a helical movement of the first scale drum 10.

Figure 9:
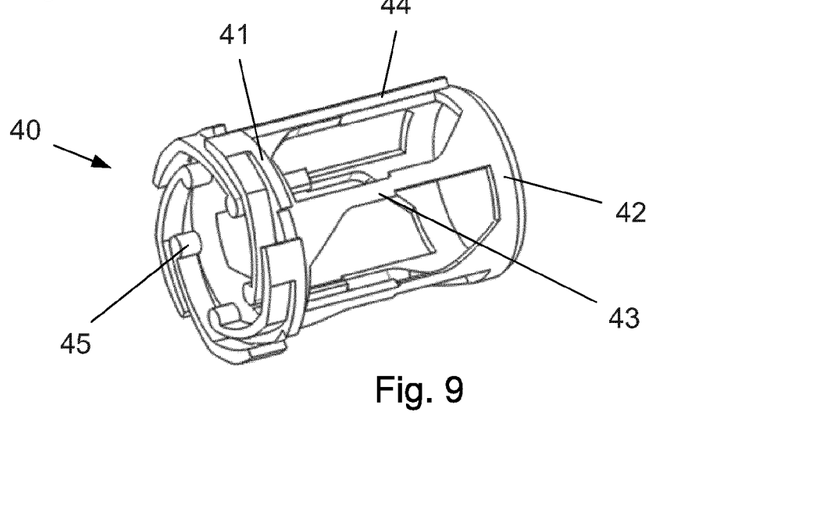
FIG. 9 show a perspective view of the clutch sleeve.

The first scale drum 10 is coupled to a clutch sleeve 40 which is disclosed in details in FIG. 9. This clutch sleeve 40 comprises of a distal ring 41 and a proximal ring 42 connected by a number of beams 43. In this embodiment the number of beams 43 is five, however any number of beams can be utilized as will be understood later.

One or more of the beams 43 is further provided with an extension 44 which engage a corresponding track (not shown) in the inner wall of the first scale drum 10 such that the second scale drum 10 is forced to rotate whenever the clutch sleeve 40 is rotated. However, the first scale drum 10 can slide axially on the clutch sleeve 40.

In order to rotate the first scale drum 10 every time the second scale drum 20 has rotated two full revolutions a clutch mechanism which will be further explained has been developed.

Figure 10:
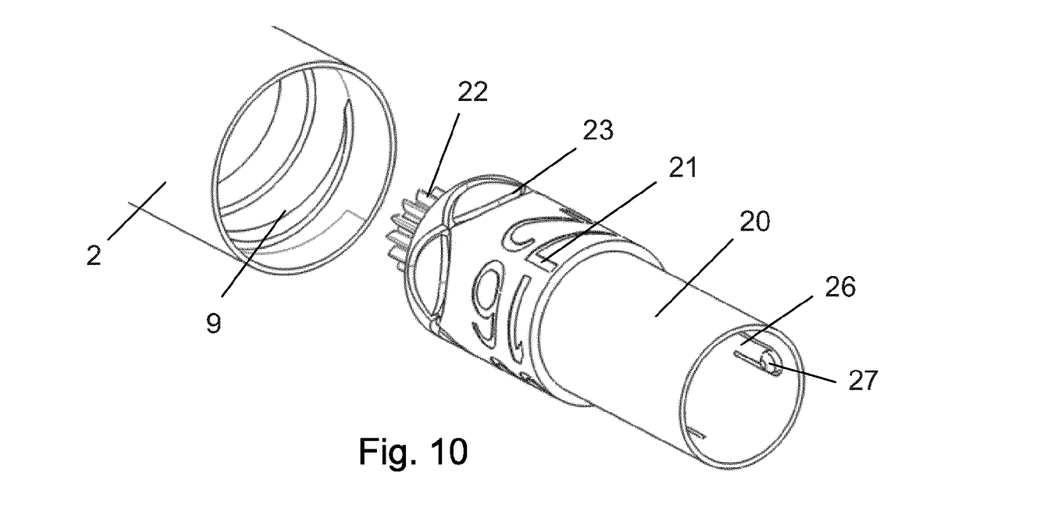
FIG. 10 show an exploded view of part of the mechanism

As depictured in FIG. 10 and in FIG. 2-3, the second scale drum 20 is provided with a clutch pin 26. This clutch pin 26 is moulded together with the remaining part of the second scale drum 20 but has on its internally pointing wall a protrusion 27 pointing inwardly (as seen in FIG. 10). Whenever this protrusion 27 is subjected to a force internally in the second scale drum 20, the outside surface of the clutch pin 26 raises above the outside surface of the second scale drum 20.

A clutch guide 50 is rigidly provided internally in the housing 2. The clutch guide 50 is firmly secured to the housing 2 without any possibility of moving. The clutch guide 50 has on its outside surface one or more raised guide bars 51.

Whenever the clutch pin 26 of the second scale drum 20 passes over the guide bar 51, the internally pointing protrusion 27 of the guide pin 26 is pushed radially outward which lifts the outside surface of the clutch pin 26 above the outside surface of the second scale drum 20.

In the position in which the guide pin 26 is lifted it can engage one of the beams 43 on the clutch sleeve 40 and thereby bring the clutch sleeve 40 with it in its rotation. This simultaneous rotation of the second scale drum 20 and the clutch sleeve 40 is transferred to the first scale drum 10 through the engagement of the extension 44 with the first scale drum 10.

Figure 12:
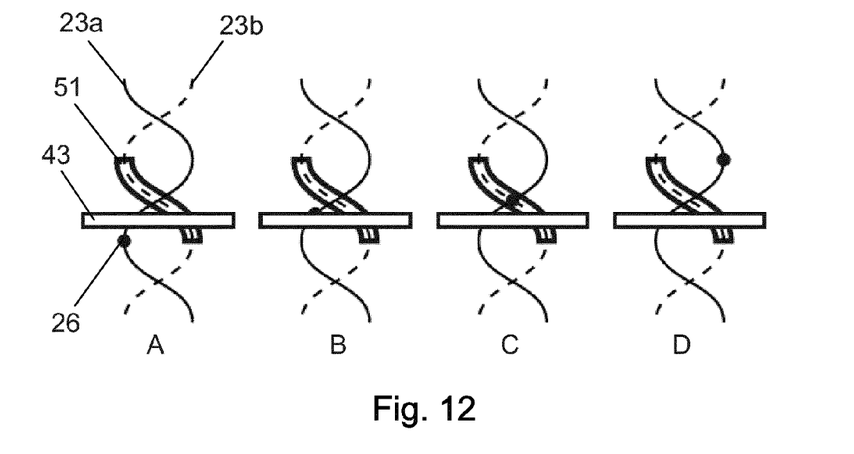
FIG. 12 show the relation between the clutch pin, the track and the beam after the first full rotation of the second scale drum when shifting from "4" to "5" in FIG. 11A.

The performance of this joint rotation is further explained with reference to FIG. 12 and FIG. 13.

The guide bar 51 on the clutch guide 50 is curved in accordance with the track 23 of the second scale drum 20 such that when the second scale drum 20 has been rotated one full revolution the guide bar 51 is out of synchronisation with the beam 43 as depictured in FIG. 12A-D. When the guide pin 26 is lifted it is thus in a location after having passed the beam 43 such that the beam 43 is not moved at all.

Since the endless track 23 oscillates following the curve depictured in FIG. 11A, the track 23 can in the view shown in FIG. 12A-D and in FIG. 13A-E be seen as having a first curve 23a and a second curve 23b. The raised guide bar 51 has a shape following one of the first curve 23a or second curve 23b.

After one full rotation of the second scale drum 20, the ciphers shifts from "4" to "5" as seen in FIG. 11A. In this position, the guide pin 26 is moved under the beam 43 as depictured in FIG. 12 and over the raised guide bar 51 as the guide pin 26 follows the first curve 23a and the raised guide bar 51 stretches along the second curve 23b. It can be seen in FIG. 12C that the guide pin 26 is raised by the guide bar 51 in a position after having passed the beam 43, the beam 43 therefore remains in its position.

Figure 13:
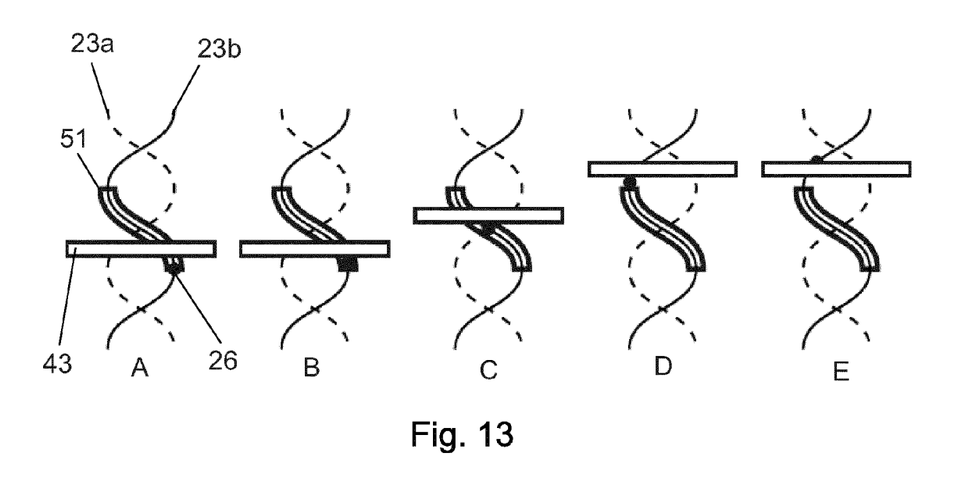
FIG. 13 show the relation between the clutch pin, the track and the beam after the second full rotation of the scale drum when shifting from "9" to "0" in FIG. 11A.

FIG. 13A-E discloses the mechanism when the second scale drum 20 has rotated two full rotations equal to 720 degree. In FIG. 13A, the guide pin 26 approaches the beam 43 following the second curve 23b going from "9" to "0" in FIG. 11A. Since the raised guide bar 51 stretches along the second curve 23b, the guide pin 26 will be lifted as it moves into engagement with the beam 43. Since the guide pin 26 is lifted it will rotate the beam 43 (FIG. 13 B-D) and thus move clutch sleeve 40 one increment thereby also rotating the first scale drum 10 one "tens" cipher up the scale. The rotational movement of the first scale drum 10 will be helical due to the engagement with the helical thread 9 internally in the housing 2.

As depictured in FIG. 2-3 and in FIG. 9, the clutch sleeve 40 is at its distal end provided with a number of flexible arms 45 which at their free ends engages a toothed ring 52 provided in the clutch guide 50. This arrangement supports that the clutch guide 50 and thereby the first scale drum 10 rotate in incremental steps.

In the embodiment disclosed in FIG. 2-3 and FIG. 9, the clutch guide 40 and the first scale drum 10 rotate a total of five incremental steps for each full revolution which is therefore the number of beams 44 and flexible arms 45 disclosed. This makes it possible for each of the first ciphers 11 to have a height of one fifth of 360 degree of the circumferential perimeter and thereby the same size as the second cipher 22. Some preferred embodiments have been shown in the foregoing, but it should be stressed that the invention is not limited to these, but may be embodied in other ways within the subject matter defined in the following claims. Should anybody e.g. want to add an extra cipher such that numbers up to "999" can be displayed the principles described above can be utilized. Alternatively, a further cipher which can only shift between "0" and "1" can be provided such that any cipher from "0" to 199" can be displayed,

The invention claimed is:

1. An injection device for injecting multiple settable doses of a liquid drug having a mechanical dose size display, which injection device comprises:

a housing having a window for displaying the size of the set dose, a first scale drum carrying a series of first ciphers and surrounding a second scale drum carrying a series of second ciphers, both the first scale drum and the second scale drum being rotatable mounted relatively to the housing, a rotational dose setting member for transferring rotation to the second scale drum during dose setting and structure for transferring rotation from the second scale drum to the first scale drum, wherein, one of the first ciphers and one of the second ciphers are visible through the window at the same time, the second cipher being visible through an opening in the first scale drum and wherein, the first scale drum is helical guided via a helical track engagement such that the first scale drum move helically during rotation and the second scale drum is axially guided via an oscillating track engagement such that the second scale drum oscillates axially during rotation.

2. An injection device having a mechanical dose size display according to claim 1, wherein the second ciphers are located in a plurality of axially displaced rows.

3. An injection device having a mechanical dose size display according to claim 2, wherein the plurality of rows is two and that each of the rows consist of five ciphers.

4. An injection device having a mechanical dose size display according to claim 1, wherein the first ciphers are helically located on the first scale drum.

5. An injection device having a mechanical dose size display according to claim 1, wherein the first scale drum is provided with a plurality of helically located openings located adjacent the first cipher.

6. An injection device having a mechanical dose size display according to claim 1, wherein the structure for transferring rotation from the second scale drum to the first scale drum comprises a clutch sleeve which is keyed to the first scale drum and configured to engage with the second scale drum.

7. An injection device having a mechanical dose size display according to claim 6, wherein the clutch sleeve and the first scale drum are rotated together one increment for each two full rotations of the second scale drum.

8. An injection device having a mechanical dose size display according to claim 6, wherein the second scale drum is provided with at least one guide which engages the clutch sleeve.

9. An injection device having a mechanical dose size display according to claim 8, wherein the clutch guide is provided with a number of beams engageable by the guide when lifted by a raised bar provided on a clutch guide secured in the housing.

10. An injection device having a mechanical dose size display according to claim 9, wherein the raised bar stretches along a part of the oscillating track.

\* \* \* \* \*